United States Patent [19]

Swor

[11] Patent Number: 4,969,893
[45] Date of Patent: Nov. 13, 1990

[54] DISPOSABLE SUTURE CUTTER AND NEEDLE HOLDER

[76] Inventor: G. Michael Swor, 4485 S. Shade Ave., Sarasota, Fla. 34231

[21] Appl. No.: 367,423

[22] Filed: Jun. 16, 1989

[51] Int. Cl.⁵ .................................................. A61B 17/04
[52] U.S. Cl. ..................................... 606/232; 30/232; 606/138
[58] Field of Search ................................ 606/222–232, 606/138; 206/370–373; 223/109 R; 30/232

[56] References Cited

U.S. PATENT DOCUMENTS

| | | | |
|---|---|---|---|
| 1,020,333 | 3/1912 | von Daam | 223/109 R |
| 1,971,814 | 8/1934 | Genda | 30/232 |
| 2,058,340 | 10/1936 | Miller | 223/109 R |
| 3,933,286 | 4/1976 | Karkas | 223/109 R X |
| 4,414,908 | 11/1983 | Eguchi et al. | 606/147 X |
| 4,726,371 | 2/1988 | Gibbens | 30/232 X |
| 4,730,725 | 3/1988 | Marshall, Sr. et al. | 206/380 X |

*Primary Examiner*—Robert A. Hafer
*Assistant Examiner*—Lynda M. Cofsky
*Attorney, Agent, or Firm*—Charles J Prescott; Raymond H. Quist

[57] ABSTRACT

A disposable suture cutter and needle holder for a suture needle having thread thereon has a supporting base for a foamed plastic needle holder. A cutting blade having foamed plastic disposed adjacent to it is also mounted on the supporting structure. In one embodiment the supporting structure is in the form of a bracelet having a reversely turned portion at one end. The cutting blade is embedded in the reversibly turned portion. In another embodiment, two truncated conical members are joined at one side of their edges and spaced at the opposite side. The cutting blade is disposed between the spaced edges. In still another embodiment, two conical members are spaced from each other by foamed plastic having diametrically opposite located slots therein. The cutting blade has cutting edges adjacent to each slot.

9 Claims, 3 Drawing Sheets

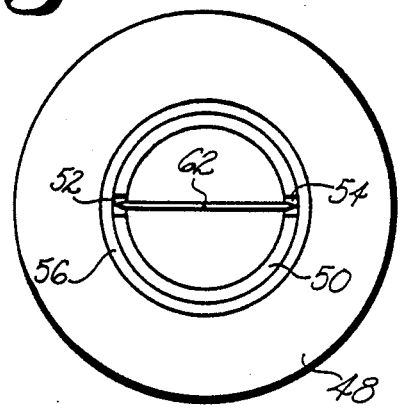
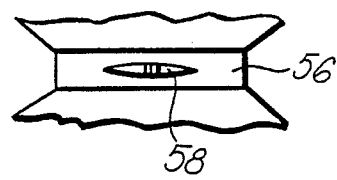
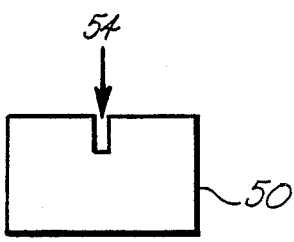
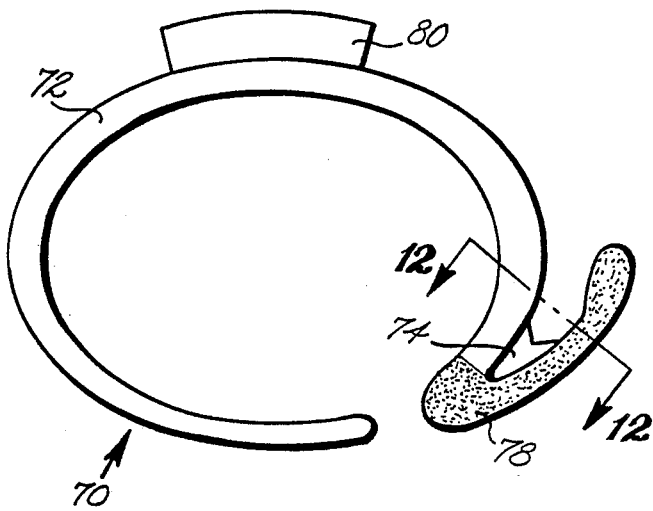
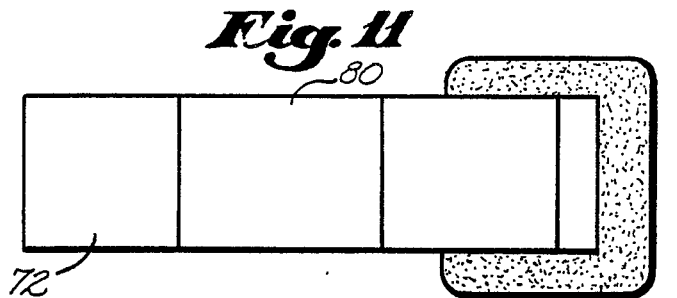
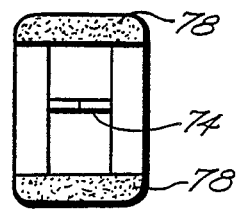

DISPOSABLE SUTURE CUTTER AND NEEDLE HOLDER

BACKGROUND OF THE INVENTION

1. Field of the Invention

This invention relates to a device for cutting the thread after a suture is formed to separate the needle from the thread and to hold the needle.

2. Description of Related Art

A suture is formed by passing a needle, having thread attached thereto, through adjacent edges of a wound or incision and then forming a knot in the thread while the edges are held together. The thread is then cut to separate the needle. It is common practice for the surgeon to rest the needle on his wrist or the back of his hand to change hand positions or while tying the knot. Occasionally, the surgeon inadvertently pricks himself while doing this, presenting the possibility of infection. There is a need, consequently, for a safe place to put the needle temporarily while keeping it near at hand. Moreover, resorting to a scissors to cut the suture thread is time consuming, suggesting the need for a more readily available cutting device.

U.S. Pat. No. 4,069,825, Akiyama, entitled "Surgical Thread and Cutting Apparatus for the Same", discloses a thread for ligating blood vessels and a trigger operated cutter.

U.S. Pat. No. 4,452,246, Bader et al., entitled "Surgical Instrument", discloses a needle holder for suturing which also includes scissor blades to cut the suture thread.

U.S. Pat. No. 4,478,221, Heiss, entitled "Instrument for Use in Surgery", discloses a clamp for retaining a needle and thread and also includes cutting means.

None of the foregoing patents discloses a provision for safely temporarily holding a needle.

SUMMARY OF THE INVENTION

A disposable suture cutter and needle holder is provided with an adhesive base for securing it in a position where it is readily available. This may be on the back of the hand or wrist of the surgeon or on the surgical drape which is positioned about the area to be treated. An alternative embodiment is in the form of a bracelet which is worn on the wrist of the surgeon. Each device has one or two suture cutting blades disposed so as to avoid any accidental cutting of the user or patient. Associated with the blade is a mass of foam or the like which will secure the thread on one side of the blade while the thread is forced in on the other side of the blade. Another mass of foam or the like is disposed to permit the point of the needle to be embedded therein for temporarily holding the needle safely.

It is therefore an object of this invention to provide a suture cutter and needle holder which can be located near to the point of use.

It is a further object to provide a suture cutter which can be used using only one hand.

In accordance with these and other objects, which will become apparent hereafter, the instant invention will now be described with reference to the accompanying drawings.

BRIEF DESCRIPTION OF THE DRAWINGS

FIG. 7 is a cross-section taken on the line 7—7 of FIG. 5.

FIG. 8 is a detail side view of FIG. 5.

FIG. 9 is a component of the suture cutter and needle holder of FIG. 5.

FIG. 10 is a plan view of another embodiment of a suture cutter and needle holder in accordance with the invention.

FIG. 11 is a side elevation of the suture cutter and needle holder of FIG. 10.

FIG. 12 is a cross-section taken on the line 12—12 of FIG. 10.

DETAILED DESCRIPTION OF THE INVENTION

Figure 1:
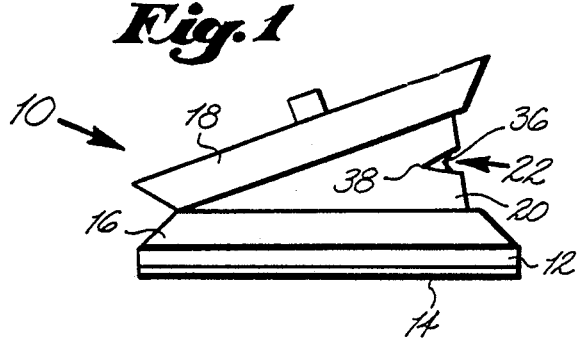
FIG. 1 is a side elevation of a suture cutter and needle holder in accordance with the invention.
Figure 2:
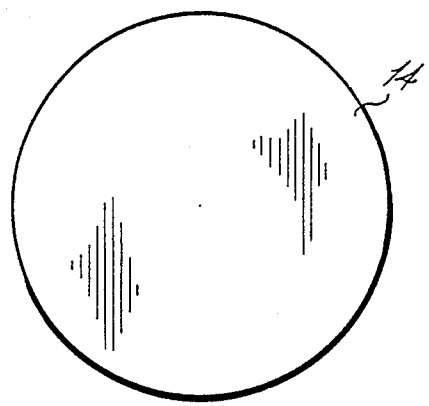
FIG. 2 is a bottom view of the suture cutter and needle holder of FIG. 1.
Figure 3:
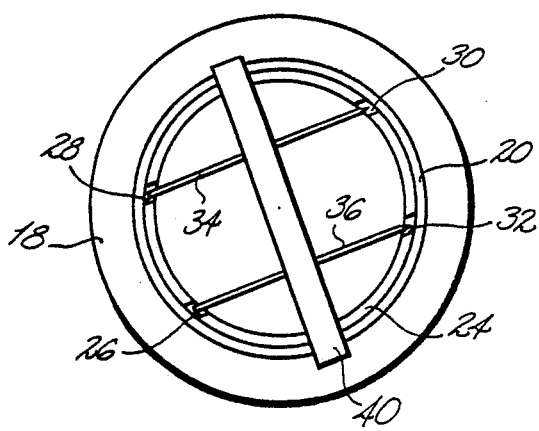
FIG. 3 is a plan view of the suture cutter and needle holder of FIG. 1 taken orthogonally to the top.

Referring now to FIGS. 1-4, suture cutter and needle holder 10 has base 12 with an adhesive bottom surface. The adhesive surface is covered with removable cover sheet 14 which is removed when suture cutter and needle holder 10 is to be used at the time of suturing. Secured to base 12 is hollow rigid plastic member 16 which is configured as a truncated cone. A similar truncated hollow member 18 is joined to member 16 at an angle. Disposed within members 16 and 18 is wedge-shaped, cylindrical foam member 20. Foam member 20 has slot 22 which extends across the highest portion of foam member 20. Foam member 20 is held in position by wedge-shaped sleeve 24. Sleeve 24 includes slots 26, 28, 30 and 32 for receiving blades 34 and 36. The cutting edge of blade 34 is disposed in slot 30, and the cutting edge of blade 36 is disposed in slot 32. As best seen in FIG. 1, the cutting edge of blade 36 is located adjacent to slot 22. The cutting edge of blade 34 is similarly located. By the arrangement described, a suture thread can be brought across slot 22 and will be held by the narrow edge 38 of foam member 20 while it is forced against the cutting edge of blade 36 and severed. This can be accomplished with one hand. Blades 34 and 36 are held in position within slots 26-32 by foam member 40 which is secured to rigid plastic member 18, as by glue. Foam member 40 also serves as the needle holder by merely inserting the point of the needle therein. It will be noted that the arrangement shown permits the suture thread to be brought across from either side. It will be apparent that a single centrally located blade could alternatively be used.

Figure 4:
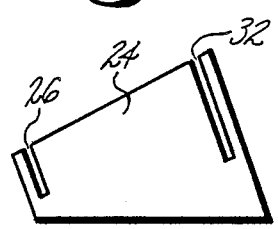
FIG. 4 is a side elevation of a component of the suture cutter and needle holder of FIG. 1.
Figure 5:
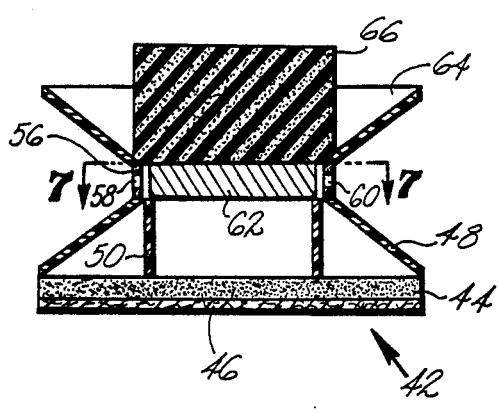
FIG. 5 is a cross-sectional elevation taken on the line 5—5 of FIG 6 of another embodiment of a suture cutter and needle holder in accordance with the invention.
Figure 6:
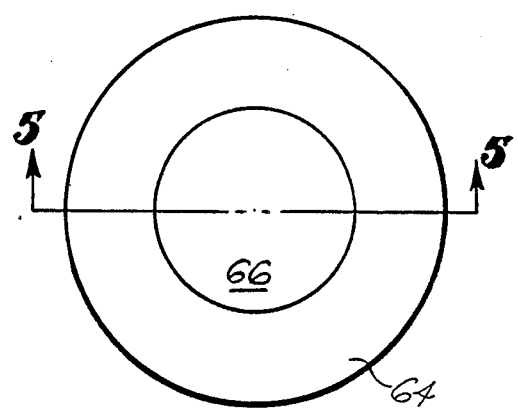
FIG. 6 is a plan view of the suture cutter and needle holder of FIG. 5.
Figure 15:
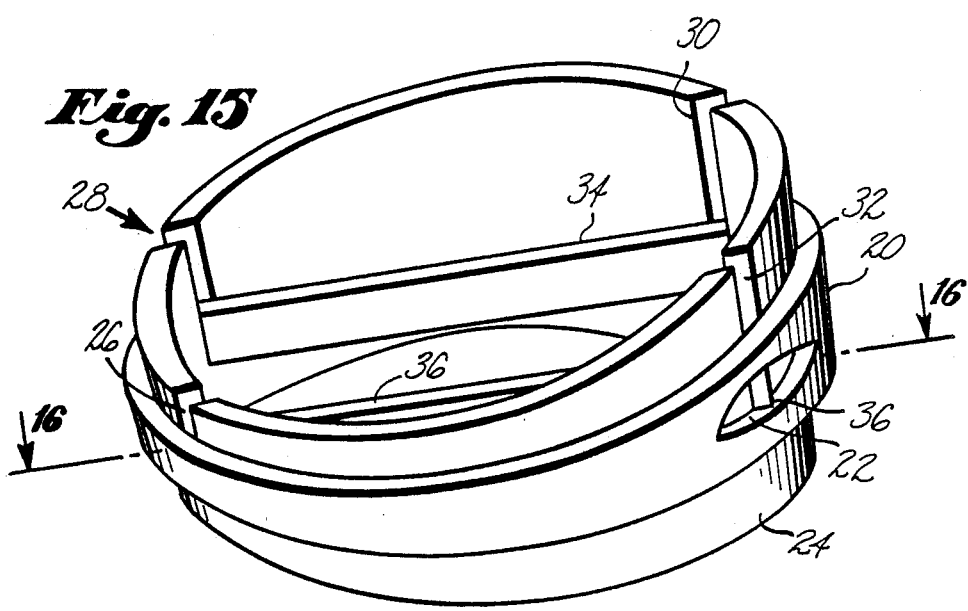
FIG. 15 is a perspective view of the component of FIG. 4 with additional components added.
Figure 16:
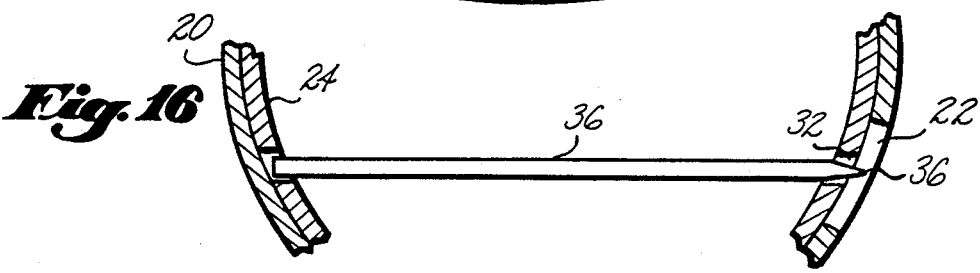
FIG. 16 is a detail plan view cross-section taken on line 16—16 of FIG. 15.

The relationship of sleeve 24 of FIG. 4 to the other components is more clearly shown in FIGS. 15 and 16. Foam member 20 surrounds sleeve 24 and maintains blades 34 and 36 in position in slots 28 and 30, and 26 and 32 respectively.

Turning next to the embodiment of the invention depicted in FIGS. 5 through 9, suture cutter and needle holder 42 has base 44 with an adhesive bottom surface. The adhesive surface is covered with removable cover sheet 46. Secured to base 44 is hollow rigid plastic member 48 which is configured as a truncated cone. Also on base 44 is sleeve 50 which contains slots 52 and 54 disposed diametrically opposite to each other. Sleeve 50 supports foam sleeve 56. Foam sleeve 56 includes slots 58 and 60 which are adjacent to slots 52 and 54 of sleeve 50. Blade 62 is supported in slots 52 and 54 and has cutting edges at both ends. Top truncated cone 64 is positioned above foam sleeve 56. Secured to top truncated cone 64 is foam mass 66 which serves as the needle holder as well as holding blade 62 in position. Having suture thread cutting edges at opposite sides facilitates cutting from either direction.

Figure 13:
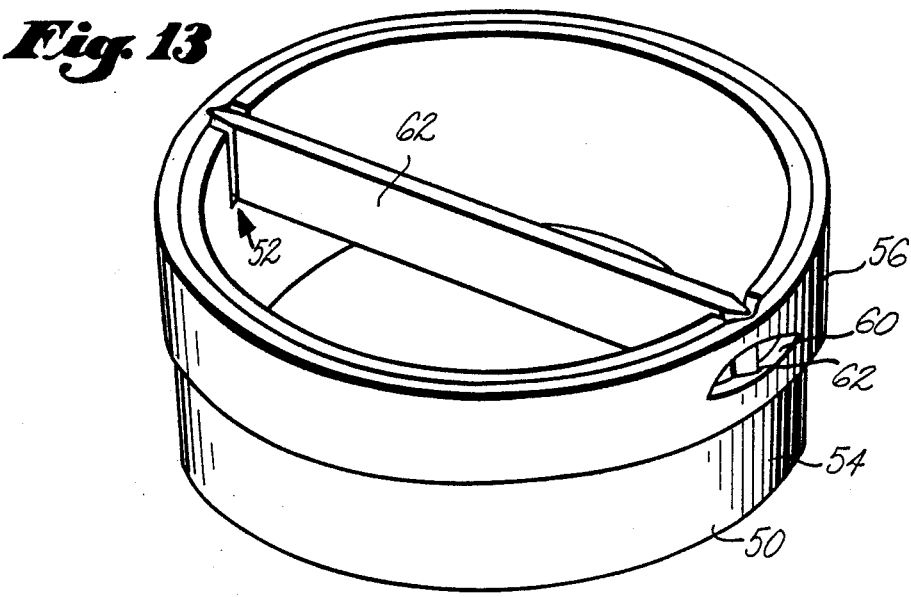
FIG. 13 is a perspective view of the component of FIG. 9 with additional components added.
Figure 14:
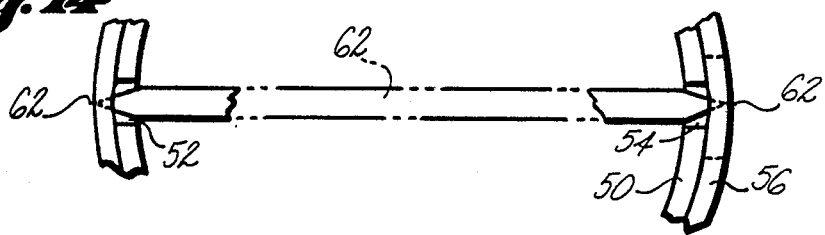
FIG. 14 is a detail plan view of a portion of FIG. 13.

The relationship of sleeve 50 of FIG. 9 to the other components is more clearly shown in FIGS. 13 and 14. Foam sleeve 56 surrounds sleeve 50 and holds blade 62 in position. Foam sleeve 56 has slots, such as slot 60 which exposes a portion of the cutting edge of blade 62.

FIGS. 10–12 show suture cutter and needle holder 70 in which base 72 is configured as a bracelet having one end with a reversely turned portion 76. Blade 74 is embedded in base 72 in the reversely turned portion and has a vee-shaped cutting edge. Foam 78 is secured to the reversely turned portion 76 to aid in cutting by holding the suture thread. An additional foam mass 80 is attached to the outside of base 72 and serves as the needle holder.

Each of the embodiments provides both a safe place to temporarily hold the suture needle and readily available cutting edges with associated thread holding foam for cutting the suture thread. The surgeon is able, with the suture cutter and needle holder of this invention, to keep his hands adjacent to the wound or incision being sutured.

While the instant invention has been shown and described herein in what is conceived to be the most practical and preferred embodiment, it is recognized that departures may be made therefrom within the scope of the invention, which is therefore not to be limited to the details disclosed herein, but is to be afforded the full scope of the claims so as to embrace any and all equivalent apparatus and articles.

I claim:

1. A disposable suture cutter and needle holder for a suture needle having suture thread thereon comprising:
   a bracelet formed of hard plastic; said bracelet having a reversely turned portion at one end;
   a cutting blade is embedded in said bracelet at said reversely turned portion;
   a needle holder secured to said bracelet spaced from said cutting blade;
   said needle holder formed of soft material, whereby a needle may be readily placed therein and removed therefrom;
   foamed plastic secured to said bracelet and disposed adjacent to said cutting blade;
   said cutting blade positioned so suture thread can be forced against said blade to cut said thread.

2. A disposable suture cutter and needle holder for a suture needle having suture thread thereon comprising:
   a supporting structure having a base with an adhesive bottom;
   a needle holder secured to said supporting structure;
   said needle holder formed of foamed plastic, whereby a needle may be readily placed therein and removed therefrom;
   at least one cutting blade secured to said supporting structure;
   foamed plastic secured to said supporting structure and disposed adjacent to said cutting blade;
   said cutting blade positioned so suture thread can be forced against said blade to cut said thread.

3. A disposable suture cutter and needle holder in accordance with claim 2 wherein:
   said supporting structure includes a truncated conical member mounted on said base.

4. A disposable suture cutter and needle holder in accordance with claim 3 wherein:
   said truncated conical member has a peripheral edge and is joined to a second truncated conical member having a peripheral edge at one point on said peripheral edges and is spaced from said second truncated conical member at a point on said peripheral edge opposite said one point;
   said foamed plastic disposed adjacent to said cutting blade is disposed between said first and second truncated conical members;
   said foamed plastic has a slot therein;
   said cutting blade is positioned adjacent said slot.

5. A disposable suture cutter and needle holder in accordance with claim 4 wherein:
   said needle holder is disposed atop said second truncated conical member.

6. A disposable suture cutter and needle holder in accordance with claim 5 further including:
   a second cutting blade positioned adjacent said slot.

7. A disposable suture cutter and needle holder in accordance with claim 3 wherein:
   said foamed plastic disposed adjacent to said cutting blade is disposed atop said truncated conical member and includes a slot adjacent to said cutting blade;
   a second truncated conical member is disposed above said foamed plastic disposed adjacent to said cutting blade.

8. A disposable suture cutter and needle holder in accordance with claim 7 wherein:
   said needle holder is disposed atop said second truncated conical member.

9. A disposable suture cutter and needle holder in accordance with claim 8 wherein:
   said foamed plastic disposed adjacent to said cutting blade is a circular sleeve;
   said cutting blade extends diametrically within said circular sleeve;
   said cutting blade has a cutting edge at each end;
   said foamed plastic circular sleeve has a slot adjacent to each said cutting edge;
   said cutting blade is supported in slots in a rigid cylinder.

* * * * *